(12) United States Patent
Ragg

(10) Patent No.: US 11,229,554 B2
(45) Date of Patent: Jan. 25, 2022

(54) ADHESIVE FILM BANDAGE FOR MEDICAL COMPRESSION

(71) Applicant: Swiss VX Venentherapie Und Forschung GMBH, Schindellegi Gem Feusisberg (CH)

(72) Inventor: Johann Christof Ragg, Berlin (DE)

(73) Assignee: Swiss VX Venentherapie Und Forschung GMBH, Schindellegi Gem (CH)

( * ) Notice: Subject to any disclaimer, the term of this patent is extended or adjusted under 35 U.S.C. 154(b) by 1169 days.

(21) Appl. No.: 15/120,354

(22) PCT Filed: Feb. 19, 2015

(86) PCT No.: PCT/EP2015/053500
§ 371 (c)(1),
(2) Date: Aug. 19, 2016

(87) PCT Pub. No.: WO2015/124669
PCT Pub. Date: Aug. 27, 2015

(65) Prior Publication Data
US 2017/0065459 A1    Mar. 9, 2017

(30) Foreign Application Priority Data
Feb. 19, 2014   (EP) .................................. 14155794

(51) Int. Cl.
*A61F 13/00*     (2006.01)
*A61F 13/02*     (2006.01)
(Continued)

(52) U.S. Cl.
CPC ........ *A61F 13/0256* (2013.01); *A61F 13/023* (2013.01); *A61F 13/024* (2013.01);
(Continued)

(58) Field of Classification Search
CPC ................ A61F 13/0256; A61F 13/024; A61F 13/0259; A61F 13/066; A61F 15/002;
(Continued)

(56) References Cited

U.S. PATENT DOCUMENTS 4,414,970 A * 11/1983 Berry ................ A61F 13/00038
602/75
4,948,065 A *  8/1990 Zelmin .............. B65H 75/4431
242/381.6

(Continued)

FOREIGN PATENT DOCUMENTS

EP        0045592      2/1982
EP        0051935      5/1982
(Continued)

OTHER PUBLICATIONS

PCT International Search Report for PCT Application No. PCT/EP2015/053500 Dated Oct. 13, 2015.
(Continued)

*Primary Examiner* — Camtu T Nguyen
(74) *Attorney, Agent, or Firm* — Medler Ferro Woodhouse & Mills PLLC

(57) ABSTRACT

The present invention relates to a transparent elastic compression bandage film composite for the treatment of venous diseases and tissue lesions, comprising a transparent film layer of 5-50 microns thickness, a medical adhesive coated on at least a portion of one surface of the film layer, which is preferably hypoallergenic, a first release liner for longitudinal detachment covering the adhesive film surface and, optionally, a second release liner for longitudinal detachment to serve as a carrier, wherein the effects of elasticity and of strong adhesion add to a compression quality superior to textile European standard compression media, in the main affecting superficial varicosities and long-term wearing.

16 Claims, 8 Drawing Sheets

Figure 1:
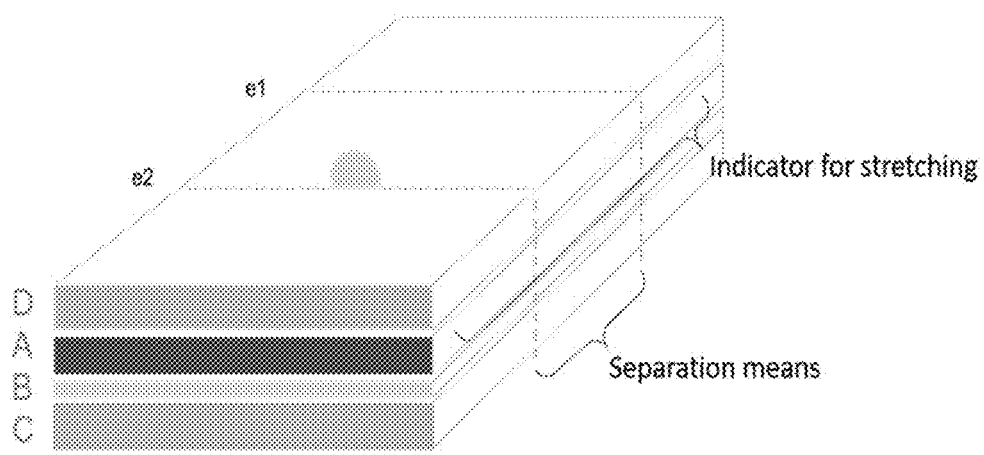

(51) Int. Cl.
  *A61F 15/00* (2006.01)
  *A61F 13/08* (2006.01)
  *A61F 13/06* (2006.01)
  *A61L 31/04* (2006.01)
  *A61L 31/06* (2006.01)
  *A61L 31/14* (2006.01)

(52) U.S. Cl.
  CPC ...... *A61F 13/0259* (2013.01); *A61F 13/0273* (2013.01); *A61F 13/066* (2013.01); *A61F 13/08* (2013.01); *A61F 15/002* (2013.01); *A61L 31/048* (2013.01); *A61L 31/06* (2013.01); *A61L 31/14* (2013.01)

(58) Field of Classification Search
  CPC ........ A61L 31/048; A61L 31/06; A61L 31/14; A61K 9/70
  See application file for complete search history.

(56) References Cited

U.S. PATENT DOCUMENTS

| | | | | |
|---|---|---|---|---|
| 5,655,450 | A * | 8/1997 | Hermannn | B65C 11/0247 101/288 |
| 5,843,011 | A * | 12/1998 | Lucas | A61F 13/023 602/57 |
| 6,103,369 | A | 8/2000 | Lucast et al. | |
| 6,142,968 | A * | 11/2000 | Pigg | A61F 13/00038 602/75 |
| 6,514,515 | B1 * | 2/2003 | Williams | A61L 27/18 424/424 |
| 6,613,347 | B2 * | 9/2003 | Drury | A61L 15/24 424/400 |
| 2003/0040691 | A1 | 2/2003 | Griesbach, III et al. | |
| 2005/0182347 | A1 * | 8/2005 | Bishop | A61F 13/0223 602/43 |
| 2011/0196329 | A1 * | 8/2011 | Eckstein | C08J 9/0061 604/369 |
| 2012/0283615 | A1 * | 11/2012 | Malik | A61L 15/58 602/52 |
| 2013/0085435 | A1 * | 4/2013 | Murphy | A61L 15/44 602/46 |
| 2013/0116645 | A1 * | 5/2013 | Corley | A61F 13/00029 604/369 |
| 2013/0344549 | A1 * | 12/2013 | Roberts | C12P 7/64 435/134 |
| 2013/0345649 | A1 * | 12/2013 | Stockley, III | A61F 7/034 604/304 |

FOREIGN PATENT DOCUMENTS

| | | |
|---|---|---|
| EP | 0673657 | 9/1995 |
| FR | 2709414 | 3/1995 |
| GB | 726747 | 3/1955 |
| WO | WO 2006/075950 | 7/2006 |
| WO | WO 2008/012443 | 1/2008 |
| WO | WO 2015/124669 | 8/2015 |

OTHER PUBLICATIONS

PCT Written Opinion of the International Search Authority for PCT Application No. PCT/EP2015/053500 Dated Mar. 30, 2015.

* cited by examiner

A B C

ADHESIVE FILM BANDAGE FOR MEDICAL COMPRESSION

FIELD OF THE INVENTION

The present invention is in the field of medicine and cosmetics, more in particular in the field of venous disease, edema and in the field of tissue injuries. The invention is also in the field of medicaments/medical devices for treating such diseases.

BACKGROUND

Several diseases, such as venous insufficiency, edema and tissue injuries are commonly treated by compression. The purpose of compression is to limit blood or fluid extravasations, hematoma, the swelling of tissue, to reduce pain, or to serve as a prevention of thrombosis by increasing the flow velocity in blood vessels while reducing their diameter. Furthermore, compression bandages can be used to fix resorptive media in a wound management.

For example, after vein surgery compression strategies follow the aims to avoid bleeding from cuts and spots where vessels or tissue have been ripped off. Second, the decrease of vessel diameters will increase the flow velocity and thus prevent thrombosis. An additional benefit is the prevention of posttraumatic swelling. In a similar way compression is applied after other kinds of surgery, like liposuction.

Varicose veins are veins that have become enlarged and tortuous. The term commonly refers to the veins on the leg, although varicose veins can occur elsewhere. Varicose veins are most common in the superficial veins of the legs, which are subject to high pressure when standing.

Besides cosmetic problems, varicose veins are often painful, especially when standing or sitting, due to blood congestion. The oxygen transfer is limited and metabolism products are locally enriched, after years of the disease skin changes like inflammations, indurations and discolorations are common. Ulcers are typical for late changes of varicose veins and venous insufficiency. Spider veins are miniature varicose veins. They are considered as a mere cosmetic problem, as far as they do not go along with other symptoms.

The treatment of varicose veins and venous insufficiency is changing to interventional techniques, which are catheter-based using laser light, radiofrequency or steam energy, or chemicals. The veins remain in the body, but are occluded and a continuous regression takes place over weeks and months until just an invisible string of connective tissue remains. Also superficial varicosities, which were surgically removed in former times, are now often also treated by interventional techniques, in particular foam sclerotherapy. After these treatments, post-interventional compression is mandatory for a couple of weeks to support and increase the process of vein regression. Furthermore, in superficial varicosities compression prevents symptomatic phlebitis, inflammatory reactions, prominent blood clots, or discolorations due to the metabolism of large amounts of clotted intravenous blood.

Figure 7:
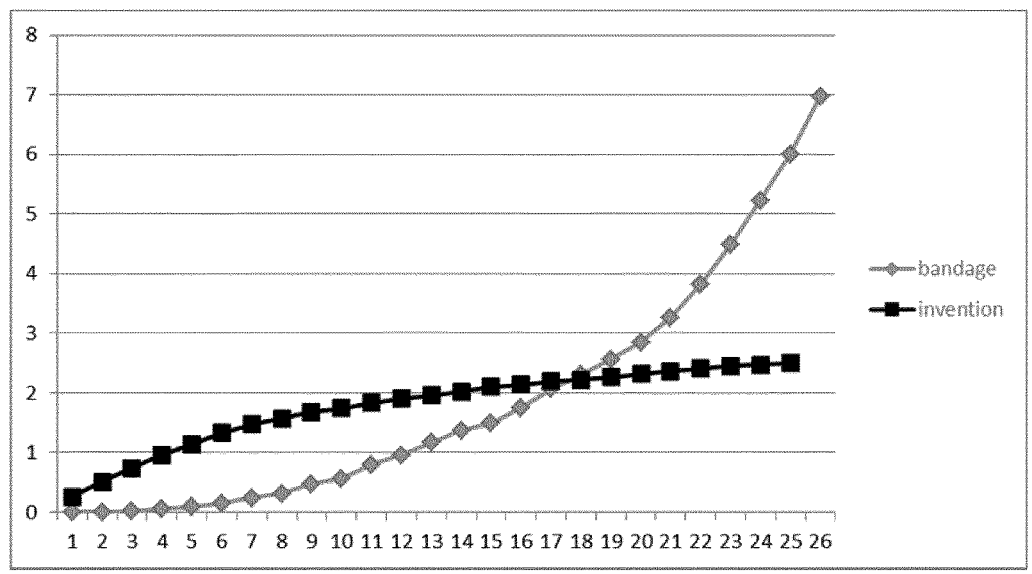

In the present medical routine, vein compression or tissue compression is performed by stockings or bandages made of woven tissue containing elastic elements like rubber or polymer fibres. Long stretch compression bandages have long stretch properties, meaning their high compressive power can be easily adjusted. They also have a higher pressure at rest and therefore usually have to be removed at night to avoid pain or discomfort. Thus, short stretch compression bandages are commonly preferred for the treatment of venous diseases. Typical stretchability is 60-90%. However, due to the low contents of elastic elements, the restoring force is weak for the first centimetres of extension, and then it will increase suddenly and rapidly unto an almost rigid behaviour due to the non-elastic elements (FIG. 7). This feature contributes to drawbacks in comfort, in particular during work or sports.

Woven bandages have to be renewed daily or every few days. For long-term treatment of venous insufficiency, compression stockings have been developed, consisting of elastic fibres or a woven compound of textile and elastic fibres. Unlike traditional dress or athletic stockings and socks, compression stockings use stronger elastics to create significant pressure on the legs, ankles and feet. However, also compression stockings usually have to be put off for the night time, as they are simply uncomfortable or even lead to ischemic pain. This is a drawback for initial use after endovenous therapy, as the loss of pressure will result in re-filling of the treated veins with amounts of blood and consecutive increase of the healing period.

Figure 5:
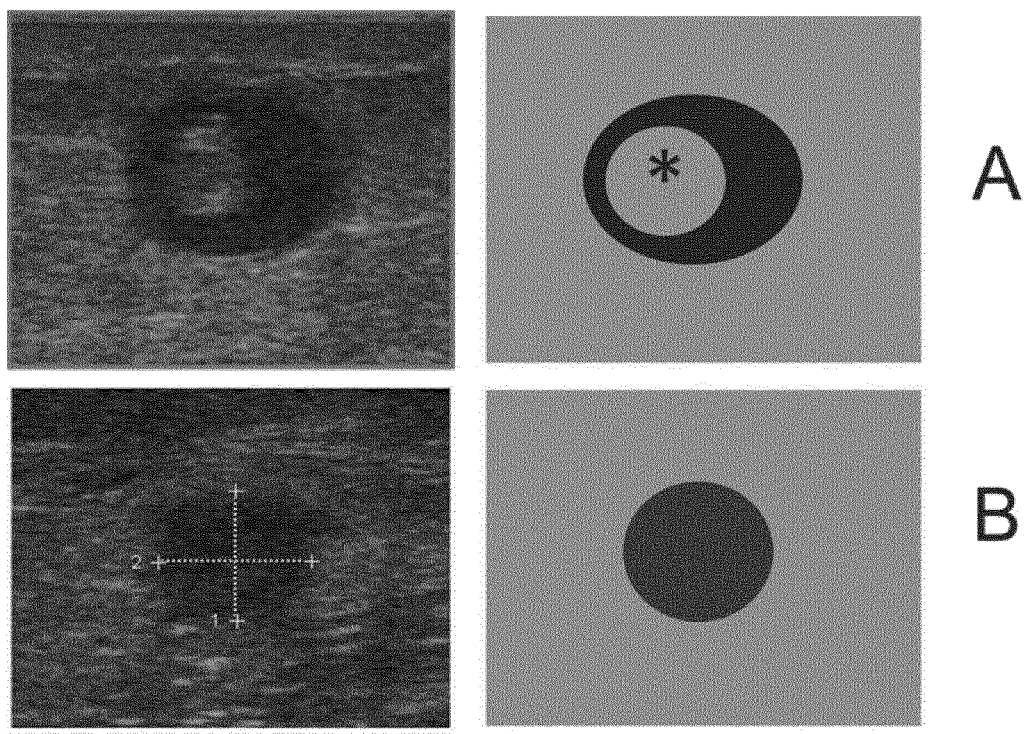

During research on vein diameters after endoluminal occlusive treatments the inventor discovered a particular ultrasound pattern, which has not been reported or explained before: The cross-section ultrasound image of occluded veins showed one circular structure of moderate signal intensity within a vein-equivalent circular structure with low signal intensity (FIG. 5). This particular pattern was present in up to 80% of the cases unto week 4, but not observed in later examinations. Normally, a homogenous cross-section signal intensity had been expected, representing blood thrombus in organization. Focusing on patients undergoing weekly examinations it could be found that this particular pattern was generated in phases of reduced compression, e.g. after removal of bandages. When the pressure exerted on treated veins is relieved, unclotted blood will enter the vein and fill the space between the existing thrombus and the vein wall, enlarging the vein diameter. The freshly arrived amount of blood will clot within the following hours and, due to its high content of water, appear with low signal intensity for a period of one to three weeks. When examining some patients every day after occlusive vein treatment, it could be found that even the pressure reduction from work to rest at night may lead to an increase in vein diameter. The conclusion is that an optimal compression modality after endoluminal occlusive treatments should provide sufficient compression as well under work conditions as under rest conditions, to avoid any re-enlargement of the vein diameter. For this purpose, the optimal compression medium has to be different from all known textile or woven media. In particular, it should be wearable for several weeks day and night without any discontinuation and without discomfort.

Veins are vessels with thin walls compared to arteries, while their diameter may be larger than in corresponding arteries. In particular, the vein's muscle layer is rather weak. Therefore, the diameter of a vein is mainly determined by the blood load or the venous blood pressure. For this reason, superficial veins are rarely seen on an elevated extremity while they are large in a drooping extremity, best seen in regions with little fatty tissue, like the back of the hand or the foot. Veins with reduced or eliminated valve competence, commonly called "insufficient", show increased diameters. In a vicious circle, valve incompetence leads to increased blood filling (congestion), and congestion further dilates the vein walls including the valve zones, provoking more valve incompetence. These are the reasons why varicosities grow with time, and why they become more and more visible. Even very large and ugly varicosities seem to normalize when the extremity is elevated over heart level for a couple of minutes. A normalization of vein diameters would mean to reduce the space consumption and therefore the pressure on the adjacent tissue including sensitive nerves (e.g. in the skin) to a normal (non-hurting) value. If a vein undergoing occlusive treatment can be normalized in diameter, there will be no more complaints due to the formerly increased vein size.

When a diseased vein is closed by means of interventional tools or injection, the amount of blood remaining in the vein or returning to that vein is decisive for the period of tissue metamorphosis.

All these methods, except endovenous gluing, do not fix the vein size during treatment, but just induce chemical or physical changes to the innermost layer of the vein, the so called endothelium. An occluded vein with denaturized endothelium will potentially lose its vascular structure and transfer to a connective tissue string. The higher the amount of blood within the vein, the more blood has to be organized and removed by the body which happens in an inflammation-like reaction. Therefore, the patient will hardly feel these changes in small veins, but most likely in large veins. As the distance to nerve containing structures is decisive for the intensity of pain, in particular large superficial varicosities which are close to the skin are subject to symptomatic vein reactions after endovenous treatments. This relation is the main reason why a new compression modality is required for vein-occluding modalities except gluing. The general recommendation to use compression stockings or bandages after any kind of vein therapy addresses quite other purposes, like the risk of thrombosis or phlebitis, and the prevention of bleedings or edema. It does not meet the requirements of interventional, ultrasound-based treatments. In particular, the benefit of continuous wearing is lost in most of the cases as patients at least want to take of the compression media for the night time or to take a bath or shower. In those periods, even when short, blood will return to the treated veins, enlarge them and extend the period and increase the symptoms of vein regression. A compression medium which allows permanent wearing could therefore help to avoid these problems.

There are several other disadvantages of common compression media. Stockings of adequate medical pressure are difficult to put on, and many patients will not be able to accomplish this without a helping hand. Bandages, on the other hand, are easy but time-consuming in their application, and the pressure will depend on the tension applied. Stockings and bandages will remove fluid and fat from the skin and make it more fragile to lesions, inflammations or infections. Therefore, stockings are usually removed in the evening to allow the skin to restore. The comfort of compression stockings, trousers or bandages is low (pain by pressure, skin abrasion by moving wrinkles; displacement, allergic reactions). Even stockings individually tailored for the patient often do not fit optimally. Bandages often cannot be worn in regular shoes as the layers are too thick. In summer times, heat congestion is frequent and makes compression media even more uncomfortable. This is a main reason why venous surgery is usually not performed in summer. One final disadvantage is the ugly appearance of bandages and medical stockings, often disclosing patients from wearing skirts or short trousers, or to participate in sports, swimming or beach live. As a consequence of all these disadvantages, the patient compliance is poor.

The compression effect of woven textile material on veins in upright standing individuals cannot be measured by imaging techniques, except in rare vertical MRT. If a compression medium could be manufactured as a transparent film, the effects on superficial veins could be visually estimated. If the material furthermore was transparent to ultrasound, the compression effect on certain veins could be directly measured in ultrasound images. This would be advantageous after vein treatments, before the patient is dismissed or as a control during follow-up.

When transparent cling film sheets are used to tightly wrap a leg with varicose veins, the film will visibly reduce the space available for the veins to dilate. The film will fix superficial varicosities to almost skin level. The more the varicosities formerly exceeded the skin level, the more their lumen size will be reduced. However, cling film sheets will slip and crumble during patient movements even when fixed with adhesive tape.

The inventor unexpectedly found that when using thin elastic semipermeable films and medical glues to tightly fix the films on human skin with varicose veins for two weeks, the diameter reduction of the diseased veins was significantly higher than by use of common woven compression bandages (Table 1).

TABLE 1

Mean diameter (mm) of varicose veins before and after sclerofoam therapy with compression media worn for 14 d in 60 randomized patients

| Movement | n | before | 14 d | 28 d | 90 d |
|---|---|---|---|---|---|
| Conventional compression bandage* | 10 | 7.2 | 5.3 | 5.6 | 4.4 |
| Conventional compression bandage** | 10 | 7.4 | 4.5 | 5.1 | 4.1 |
| Compression bandage short stretch*** | 10 | 7.3 | 5.1 | 5.5 | 4.5 |
| Compression bandage short stretch**** | 10 | 7.2 | 4.6 | 5.0 | 4.0 |
| Adhesive compression film bandage***** | 20 | 7.3 | 3.9 | 4.2 | 3.1 |

Figure 2A:
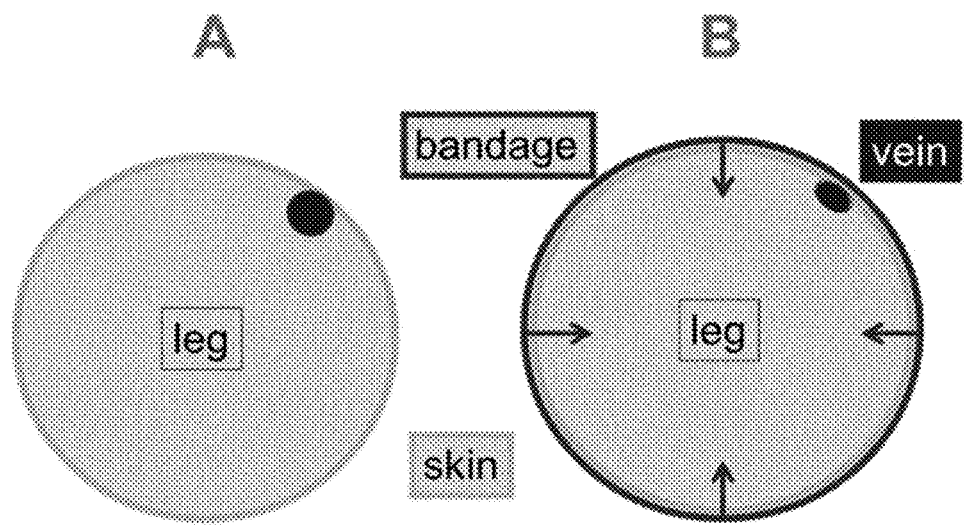
Figure 2B:
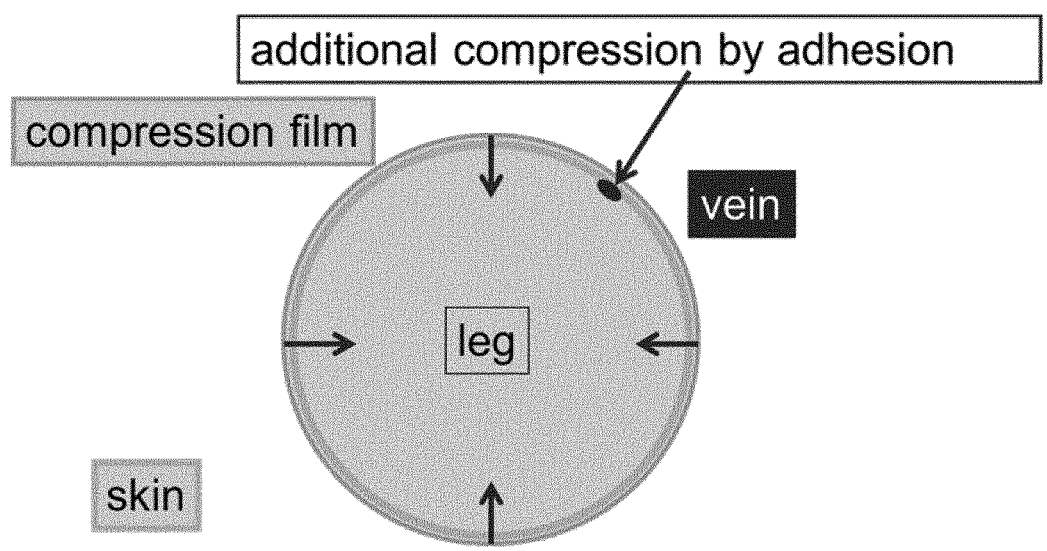
Figure 8:

*Sigvaris, class 2 Germany, 24 h + daytime
**Sigvaris, class 2 Germany, 14 day + night
***bandage 24 h + daytime
****bandage day and night, renewed every 2-3 days
*****day and night Investigating this effect on varicose veins, it could be found that there are three forces contributing to the vein compression by adhesive elastic films:

A) orthogonal forces defined by the adhesive strength of the glue alone by limiting the available space. This applies in particular to superficial veins (FIGS. 3d-e, 8). For an accurate physical description it has to be mentioned that the space-limiting effect of the glue is reduced by the stretchability of the film for a low percentage. For instance, if a compression tape is applied on an elevated leg, its varicose veins will be fixed in a collapsed condition, even when the film has no elastic properties;

B) forces defined by the film's resistance to shear stress due to the adhesive, as the adhesive film is not able to slide on the skin. This may be explained using the previous example: When the circumference of a leg increases when changing from elevation to a drooping position according to blood inflow, any conventional bandage will slip on the skin to adapt its length. However, the adhesive film bandage will not slip due to the adhesive and thus resist the shear stress (FIG. 3d-e);

C) the well known centripetal force by concentric compression, depending on the pre-tension of the compression medium during attachment (FIGS. 2b, 3e). This force is different for conventional media and a compression film, because the woven textile media just contain a percentage of elastic media, while the compression film can be completely manufactured from elastic material.

For these reasons, the desired effect of a compression film bandage has to consist of these 3 components and can only be established by particular mechanical properties of the glue and the film according to the invention. Furthermore, the compression film bandage requires certain backings or release liners for storage and delivery, as in the most embodiments the thin adhesive film is too floppy as to handle it manually without supportive media.

Comparing the compression effect of an adhesive compression film bandage and conventional textile media, its effect is different. In those well-known media the compression effect is due only to the elastic properties of the tissue, as the material does not stick to the skin. Using a self-adhesive compression bandage film means to establish a compound of film and skin (FIG. 3e). Other than with a textile bandage, the material cannot slide on the skin or on itself. As soon as the film is adhering to the skin, the elastic properties of film and skin—and even with influence of the underlying connective tissue—will add. For this reason, the pressure effects on target structures like veins have always to be understood as a result of film and glue properties plus properties of the skin and connective tissue. In result, when using the compression film bandage there is an additional general constrictive force (C) and a particular constrictive force on superficial varicose veins above skin level, due to the adhesive properties of the film (A, B).

This quality, summarizing the influence of adhesive and film elasticity, can best be defined by the resulting changes in vein size (FIGS. 2, 3). The general compression effect due to the elastic properties, similar to the concentric effects of conventional compression stockings or compression bandages is defined best by the achieved increase in tissue pressure. This is also the common basis for conventional compression media and for the definition of "compression classes", even when the nomenclature may be different from country to country (table 2).

TABLE 2

Ankle pressures of compression classes I-II in mmHg in international comparison (Rabe et al., 2008)

| Compression class | USA | UK | France | Germany | sugg.* |
|---|---|---|---|---|---|
| I | 15-20 | 14-17 | 10-15 | 18-21 | 10-20 |
| II | 20-30 | 18-24 | 15-20 | 23-32 | 20-30 |

*sugg. = suggested values for compression film bandage, added by inventor

While no elastic film bandages have been described for the purpose of general tissue compression, some elastic dressings have been presented for different local purposes like prevention of bleedings from veins or arteries, or as a wound dressing. WO 2004/112666 discloses a bandage with an elastic compression means. The disclosure relates to a dressing comprising a swab that can be placed against the wound and absorbs secretion there from, a means for pressing the swab against a wound, and a fastening means for locally fixing the dressing. The pressing means is embodied as an open-pore or closed-pore foam material which can be deformed in an elastically reversible and delayed manner and is accommodated within the dressing between the swab and an outer cover layer that overlaps the swab.

Figure 6:
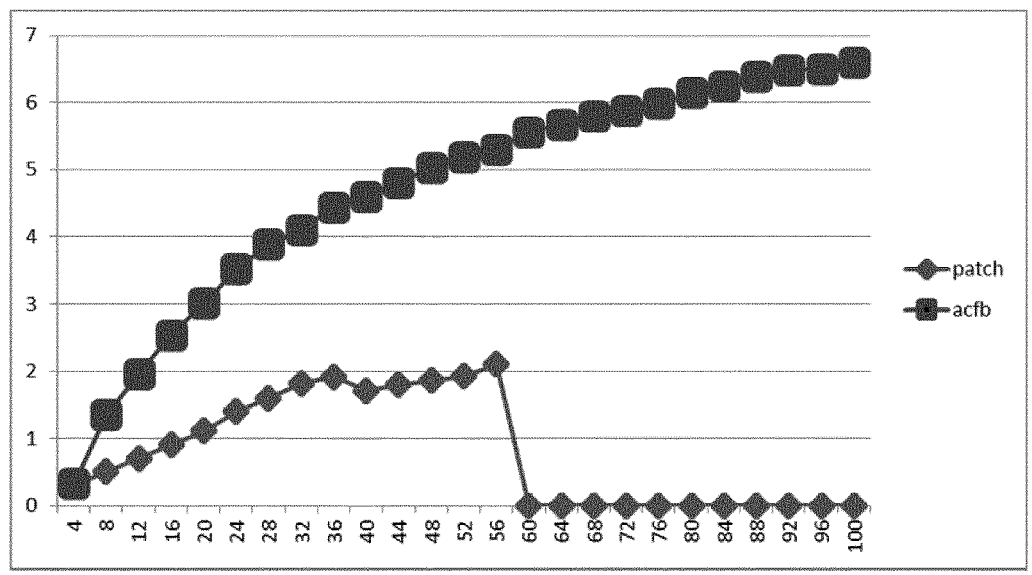

The particular mechanical features of the elastic film and glue composite according to the invention define applications in which a compression bandage film will perform better than conventional textile bandages or stockings, and different from medical films produced for wound management (FIG. 6, 7).

Band-aids or patches made from film material have been used in medicine as transparent wound covering, usually sterile, with or without additional resorptive area, in different sizes depending on the size of the wounds to treat. The use of transparent film material was mainly intended by the aims to obtain continuous view on a wound and second to have a more flexible patch to fix it in non-plain ground. In the most-spread film patches (TEGADERM®, 3M) the patch of desired size is taken from a sterile cover, a non-adhesive paper covering the glue at the bottom of the film is removed transversally, the film patch is placed on the wound and finally a second sheet is removed from the surface of the film. In this case, the surface cover is removed by grabbing two paper flags and pulling the two halves of the patch cover to the side. This kind of application is laborious and not transferable to the use as compression bandage, where the film has to be positioned continuously round by round, slightly overlapping, to a body part while holding the film under a certain tension. Furthermore, the elastic properties of such film patches are weak and just meant to adapt to any part of the body surface. They are not meant to provide concentric pressure and will fail in such attempts (FIG. 6).

The present invention does neither relate to the prevention or treatment of bleedings from arteries or veins, nor to the treatment of wounds, but to the reduction of vein diameters and to the fixation of therapy-reduced superficial vein diameters.

SUMMARY OF THE INVENTION

The present invention relates generally to an adhesive film compression bandage composite and a dispenser thereof as described herein. The adhesive composite and dispenser may be used for the compression of human tissue or in particular of human veins. As such, it may be used as a medicament, in particular for the treatment of venous or vascular diseases, such as varicose veins. Preferably, the composite is for use in regions with veins treated by interventional means like physical or chemical closure. Another use is any kind of soft tissue lesion in which external compression is considered useful to support healing. Examples are muscle fibre rupture or regions after liposuction. More preferably, the composite is for use in treating varicose veins including spider veins.

The transparent compression film bandage composite described herein comprises a thin elastic film layer, an adhesive which is preferably pressure-sensitive and hypoallergenic coated on at least a portion of the lower surface of said layer, a first release liner for longitudinal removal covering the adhesive side of the film, and, optionally, a second release liner for longitudinal removal adhered to the upper side of the film to serve as a carrier. The adhesive provides strong adhesion on the upper side of the film, and moderate adhesion on human skin. The film is permeable to vapor, transparent and allowing ultrasound transmission. The optional dispenser comprises a roll carrying the composite of adhesive film and release liners, furthermore a mechanism for proper film deployment.

DETAILED DESCRIPTION OF THE INVENTION

The optimal compression bandage modality for human body parts, in particular after endovenous procedures including sclerotherapy should be transparent to allow optical and ultrasound control of the compression effect. It should be very flexible to follow the patient's movements, and adhere tightly to the skin to avoid skin irritation. It should be very thin and permeable to vapor to provide high comfort even in permanent day and night wearing for several weeks. It should be elastic and strong enough to meet common vein compression standards, like a pressure of 10-32 mmHg at the ankle, decreasing towards the thigh. In the particular application on superficial veins bulging over skin level, it should exceed the diameter reduction obtainable by textile bandages at identical pressures.

The present invention provides a solution to all these demands of compression, in particular after interventional vein therapy. The present invention relates generally to a compression bandage film composite and a dispenser thereof, which can be applied by wrapping it around the target region like a conventional compression bandage or in closed circles, with a minimum of overlapping. In particular, the invention discloses a novel combination of material elasticity and glue properties adding their effects for an improved compression in particular of superficial veins.

The present invention may be used for the compression of human veins or tissues. As such, it may be used as a medicament, in particular for the treatment of venous or vascular diseases, such as varicose veins. Preferably, it is for use in regions with veins treated by endovenous means, e.g. physical or chemical closure. Another use is any kind of soft tissue lesion in which external compression is considered useful to support healing. Examples are muscle fibre rupture or regions after liposuction. More preferably, it is for use in treating varicose veins including spider veins.

The adhesive compression film bandage according to the invention is a transparent composite accumulating elastic and adhesive forces for the treatment of venous or vascular diseases and tissue lesions.

A film according to the invention is defined as is a thin continuous polymeric material consisting of one or several components. The term compression bandage composite includes the elastic film, the adhesive and the one or several release liners. The terms "compression film bandage" or "compression bandage film" refer to those layers which are to be applied to a patient, i.e. film and adhesive, without any release liners or application aids. According to the practical use of the adhesive compression film bandage, the side attached to the skin are referred to as "lower side", "lower surface" or "bottom side" of the film, and the opposite side of the film as the "upper side", the "surface" or "upper surface".

The composite as disclosed herein comprises several layers lying on each other (FIG. 1). The layers are (A) a thin, elastic and semipermeable film layer, (B) a medical adhesive coated on at least a portion of the lower surface of the film layer and (C) a first release liner for longitudinal removal covering the adhesive surface of the film. There may be optionally (D) a second release liner for longitudinal removal adhering to the non-adhesive side of the film to serve as a carrier, and means for longitudinal separation of one or both release liners (e1, e2).

(1a) The most important property of the film, when designed for compression purposes, is the elasticity. Elasticity is a physical behaviour of bodies that deform reversibly under stress. When an elastic material is deformed due to an external force, it experiences internal forces that oppose the deformation and restore it to its original state if the external force is no longer applied. In some objects like metallic springs the elasticity is linear according to Hooke's law. This means, the restoring force is proportional to the elongation. The restoring force is the force executed by the expanded object to return to its original size or shape.

The elastic behaviour of an expanded object is described by the modulus of elasticity, defined as the ratio of expansion to strain. Another expression for strain is tension.

Figure 4:
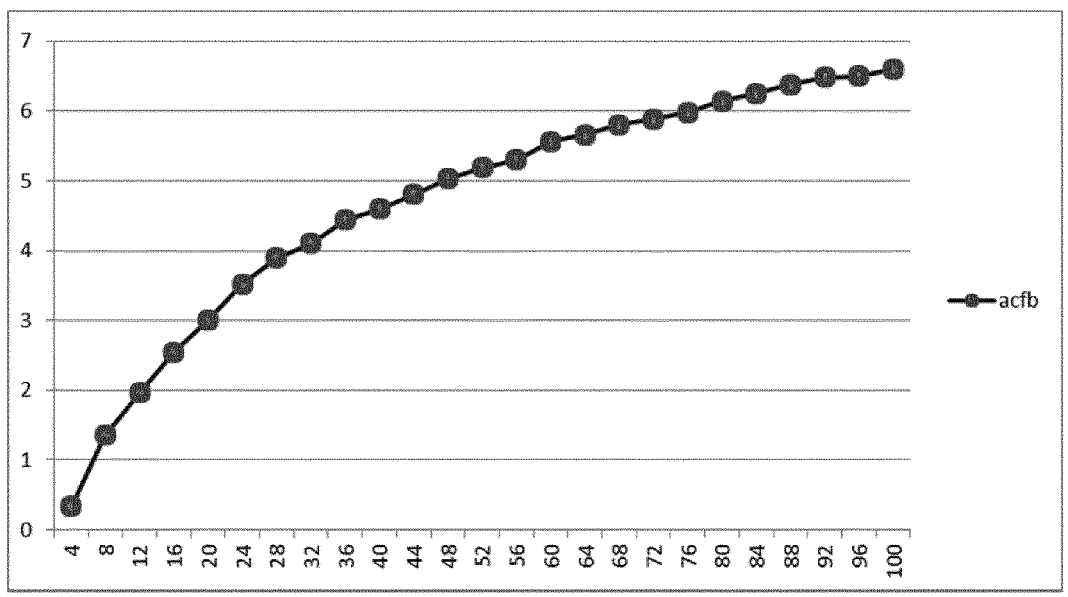

The modulus of elasticity E is defined as the slope of the graph in the tension-extension curve under uniaxial tension: $E=\sigma/\epsilon$ ($\sigma$: tension; $\epsilon$: extension elongation). Elongation or extension is defined as the ratio of the change in length as compared to the original length (unit: dimensionless, or %). E is linear for objects obeying Hooke's law. In other objects like polymeric materials the elasticity is typically non-linear, but curved (FIG. 4). In the compression film bandage according to the invention, the modulus of elasticity has an almost linear behaviour within the recommended application range with extensions of between 20 and 50% or even 10 and 75%. "Almost linear" is defined as a deviation from a linear ratio of less than 30% (FIG. 4).

The modulus of elasticity E is derived from tension-extension measurements. These were performed on film samples of 100 mm width and different lengths from 100 to 200 mm. The sample width does not influence the modulus of elasticity E or the tension-extension relation, as these refer to a force per cross section unit (e.g. $N/mm^2$).

For tension-extension measurements like mentioned within the text and as well in FIGS. 4, 6 and 7, film samples of 100 mm width were fixed at one side to a firm board while the opposite side was clamped to a 100 mm wide mount equipped with ball-bearings to roll almost frictionless on the board. Then, horizontal tension was applied while elongation (cm) was measured on a centimeter scale and forces by use of a digital dynamometer (N).

For the film according to the invention, the modulus of elasticity is 5-400 $N/mm^2$, more preferably 10-200 $N/mm^2$, most preferably 20-50 $N/mm^2$, when applying expansions of 10-100%, preferably 20-75% and even more preferably 30-50% and producing tensions of 1-40 $N/mm^2$, more preferably 2.5-25 $N/mm^2$, most preferably 5-10 $N/mm^2$;

The elastic properties of the bandage film refer as well to longitudinal direction as to transversal direction, to allow a helical wrapping fitting the anatomy of the body. For this purpose, the transversal modulus of elasticity is defined to be 25-100% of the longitudinal modulus of elasticity.

After termination of external strain on polymeric materials the initial length may not be totally obtained. This is called hysteresis. For the compression film bandage according to the invention, the hysteresis-related loss of restoring power is defined to be less than 10% in an expansion range of 20-50%. The bandage film material does not substantially lose the tendency to return into its initial length during the time and conditions used for follow-up therapy, which is typically for 7-28 days at 0-40° C.

The definition of the material's modulus of elasticity according to the invention also addresses the requirement to establish the required compression without imposing a lot of physical efforts, and to use extensions which are comfortable during application by the medical staff.

(1b) The second important property of the compression film bandage is the particular adhesive. It is essential for the function of the compression film bandage. The medical adhesive (B) is preferably pressure-sensitive and hypoallergenic. Suitable adhesives may be selected from the group of acrylates, polyacrylates, polyvinyl ethyl ethers, silicones, or others.

As there may be contact to surgical sites or puncture sites the lower surface including the adhesive is preferably sterile.

The force necessary to pull off an adhesive strip is called adhesive strength. It is often measured on a 25 mm wide strip and then has the unit N/25 mm.

The adhesive strength is usually measured on a 25 mm wide strip and then has the unit N/25 mm (mentioned within the text), and exactly this sample width was used for the measurements on the films according to the invention: 25 mm wide and 100 mm long strips were attached for 50% of their length with glues according to the invention to various human skin surfaces or to samples of film which were inseparably fixed to a board. Then orthogonal forces were applied, monitored by a digital dynamometer, until the adhesion dissolved. The force necessary to pull off an adhesive strip is called adhesive strength.

Once applied, the composite has to stick to the skin firmly enough to follow any movement of the body surface without detaching, and without formation of wrinkles. In particular, it should provide an adhesive force sufficient to prevent the bulging of superficial veins in the standing patient (FIG. 3). Bulging means any protrusion of vein parts above the skin level. Superficial means that at least parts of a vein extend above skin level. However, the adhesive should allow painless detachment of the film bandage at termination of wearing time. Therefore the adhesion to human skin is defined for the invention as performing an adhesive strength of 0.06-1 N/25 mm, more preferably 0.1-0.5, most preferably 0.12-0.25 N/25 mm, measured after 24 hours of wearing. These adhesive forces are sufficient to compress superficial varicose veins even in case of abnormal increased blood pressures up to 25 mmHg, even without any elastic properties of the bandage (FIG. 3d,e).

The adhesive strength may vary during long time wearing due to temperature and moisture and thus may exceed the defined range. It also varies with factors of the skin like fats or sweat on its surface. It is therefore recommended to remove grease and sweat before application of the bandage. Normally, this is routinely done as the body region which is subject to bandage application is also subject to invasive medical treatment and therefore washed and disinfected prior to treatment.

At the same time, the bandage film should firmly stick to its own surface, so a bandage once produced will behave and fit like a closed compound in the way of a compression stocking.

This property is defined for the invention as to provide adhesion to the upper side of the film with an adhesive force of 0.12-2 N/25 mm, more preferably 0.2-1, most preferably 0.25-0.5 N/25 mm. The demanded adhesive force is due to two factors, 1) the adhesive and 2) the kind of film surface which preferably should be very smooth and free from fat and removable particles.

It is preferred to use the compression film bandage on hair-free (shaved) skin, as the removal is easier and the adhesion is stronger. Furthermore, the film will attach to the skin closer on hairless skin, preventing water entering behind the film from the edges when the patient takes a shower.

(1c) A first release liner (C) is used as a cover for the adhesive surface of the film. Its task is to protect the adhesive from dirty or infectious particles, and to preserve the quality of the adhesive. It also provides a protection against incidental attachments prior to the intended application. Furthermore, the release liner may serve as a carrier for the very thin and floppy film. The release liner is designed for longitudinal removal during the application of the bandage.

(1d) Optionally, a second release liner (D) is used as a carrier to support the application of the film after the first release liner has been removed. This may be necessary for embodiments in which the film is too floppy as to be handled without a second carrier. The optional release liner is just softly adhering to the non-adhesive side of the film. Like the first release liner, it is also designed for longitudinal removal. To allow visual control of the film and the target region, the second release liner is preferably transparent.

In one embodiment the second release liners is non-expandable and therefore separated from the film bandage before attaching on skin or when leaving a dispenser. In another embodiment the second release liner is expanded together with the film and removed after the adhesive film is attached to the skin and before the subsequent circle of the compression film bandage is applied.

The first and second release liner may be made of paper, preferably waxed paper, or polymeric material. In some cases, both the first and the second release liner may be made of paper. In some cases, both the first and the second release liner may be made of plastic. In some further cases, the first release liner may be made of paper and the second release liner may be made of plastic, or vice versa.

The adhesive compression bandage according to 1a-d allows novel compression effects establishing a diameter reduction in superficial veins which reach or exceed the diameter reduction achieved by phlebological textile short-stretch compression bandages in identical wrappings, or adequate compression stockings (TABLE 1).

The composite and in particular the adhesive and, optionally, the film layer should be non-toxic, biocompatible and non-allergenic. The composite may optionally further comprise a superabsorbent polymer which can absorb blood. This layer may be located between the adhesive and the film layer. This layer can also comprise additives, e.g. a haemostatic compound to induce blood clotting or antimicrobial properties, or substances to promote wound healing, prevention of edema or for vein regression.

Preferably, the adhesive layer is sterile. More preferably, the adhesive and the film layer are sterile. Most preferably, the whole composite is sterile and packaged. It is preferred that the film material, in particular the upper surface, is disinfectable.

The composite according to 1a-d is capable of executing pressures of 6-32 mmHg, preferably 8-24 mmHg, most preferably 10-18 mmHg, measured as the pressure in the underlying tissue, using a single layer closed loop of the composite, measured at the ankle of an average individual.

The applied pressures may be lower than according to conventional recommendations, as the forces due to the adhesive have to be added (TABLE 1). In comparison to textile compression bandages used in phlebology, the restoring force of the film compression bandage is much higher up to 75% of the elongation (FIG. 7).

The pressure of circumferential compression media acting on a part of the body depends 1) on the elastic tension or strain of the medium and 2) on the shape of the compressed surface. For use after vein treatments, compression is meant to decrease from distal to proximal, to support the physiological venous flow which is directed towards the heart. For the compression bandages, conventional or according to the invention, this means an application providing a constant pre-tension in body parts where the diameter increases from distal to proximal. In regions with decreasing diameters, the pre-tension should be increased from distal to proximal. These considerations are based on Laplace's law, which explains the pressure exerted on a body part by an elastic material applied in a concentric way to be inversely proportional to the square of the radius of curvature. Pre-tension is defined as the tension applied on the bandage film before it is attached to the skin.

In the compression bandage film according to the invention, the pre-tension is equivalent to the aimed longitudinal strain. Typical values are 1-40 N/mm$^2$, more preferably 2.5-30 N/mm$^2$, most preferably 5-20 N/mm$^2$ Due to LAPLACE law, the pressure grows with the inverted square of the surface radius. This applies to all compression media. In manufactured stockings with a defined compression range, the compression is measured on standardized solid models with pressure sensors, but may vary when worn by a real patient. Also woven compression bandages have no means for compression control after placement, the compression effect depends on the experience of the medical personnel.

Common compression stockings are classified as class I, II or III depending on the performance of the materials and its indication for use. Severe venous hypertension is associated with edema, eczema, skin pigmentation, indurations and ulcerations and is usually object to compression classes III. The management of mild venous insufficiency and varicose veins requires compression class II, while class I is chosen for healthy subjects to prevent venous overload. The definitions of compression classes may vary from country to country (TABLE 2). The main indication of the novel compression film bandage is the application after endovenous treatments with the purpose to reduce the diameter of treated veins to accelerate their transformation to connective tissue. This indication requires lower pressures than surgical treatments. The inventor found during research on compression media that pressures of 12-22 mmHg are totally sufficient for this indication. When applying the compression film bandage, due to the additive effect of elasticity and adhesive the required pressure is 10-18 mmHg depending on the size and position of the treated veins.

The compression film bandage can be applied like a conventional compression bandage by wrapping it helically around the target region, or in single circles ("bamboo type"), with some initial, lateral and terminal overlapping and with at least one closed final circle. The term closed circle means the final part of an applied piece of film sticks on its own surface, not on the skin. Closed circles or helices are mandatory if it is the purpose to relief the skin from tension, and put the stress mainly on the bandage material.

Some initial portion of the adhesive film bandage of a few centimetres in length is freed from the first release liner and firmly attached to the distal part of the target region. Then, a further portion of the adhesive film of ½ to 1 circumference in length is freed from the first release liner, the film bandage is elongated by manual application of the desired pre-tension and then fixed on the target region in a circular or helical way. If a second release liner is involved, it is detached prior to elongation if it is non-elastic, and after attachment if it is elastic.

Preferably, the compression film bandage is applied in a single layer with a lateral overlapping of 0.5-2 cm or 5-15% of the film width. This way, the majority of the area is covered by a single layer of the bandage film allowing the semipermeable properties to work.

If required, the compression bandage film can be applied not just in one but in several layers, as imbricated work or the PÜTTER way. In this case, the elastic force of each layer will add, providing higher degrees of compression while using the same pre-tension during positioning. This way, even ankle pressures of 32 mmHg and above are achievable, which are required for post-surgical treatment (vein stripping, phlebectomy) or patients with post-thrombotic syndrome. However, the property of vapor transmission may be lost or restricted.

The defined adhesive is strong enough to produce a firm connection to the film's surface resistant to everyday movements, including extreme sports, using a lateral and terminal overlap of just 0.5-2 cm, or 5-15% of the bandage width. The skilled person will appreciate that there is not an actual maximum of the adhesion strength of the film on its own surface. Even within the defined range in (1b), the adhesive film will provide a stable compound which is able to resist tangential stress. An adhesive bond of a circular loop of the adhesive film bandage with just 0.5-2 cm terminal overlap or an overlap of 5-15% of the bandage rather leads to the tearing of the film than to a release of the adhesive bond.

The tensile strength defines the the maximum stress that a material can withstand while being stretched or pulled before failing or breaking. Concerning the compression film bandage, the tensile strength of a longitudinal overlapping adhesive zone of 0.5-2 cm is defined to be larger than the tear strength of a single film layer. This means that when stressed above the tear strength limit the film will break at any other location except the overlapping zone. This feature, depending on the adhesive strength when the film according to the invention is attached on parts of its own surface, is relevant to achieve a uniform compound of several helical or circular wraps with a minimum of overlapping. The area of overlapping zones of the compound should not exceed 15% of the covered region.

The film layer has preferably a tensile strength of 5-50 N/25 mm, more preferably 7.5 N/25 mm to 40 N/25 mm, most preferably 10 N/25 mm-30 N/25 mm.

The elongation at break indicates by how many percent a tape is extended before it breaks. The elongation at break of the film layer is preferably 100-400%, more preferably 125-300%, most preferably 150-200%.

To offer maximum wearing comfort and to support the property of semipermeability the film has to be as thin as technically feasible, limited by the demand to establish certain pressures which depends on a certain quantity of material. In particular, the restoring force of a bandage is equivalent to the cross-section of the elastic elements. According to today's technology, the composite of according to the invention is preferably 5-50 microns in thickness, more preferably 6-30 microns, even more preferably 7-20 microns. Future materials may offer even thinner layers. As the bandage has to be permeable to moisture, the microhole or micropore technology may influence the film's thickness. Any holes will weaken the elastic properties, and a larger film thickness will make semipermeability of films more difficult.

Ideally, 90-100% of the lower surface of the film layer is covered with the adhesive, preferably homogenously and in an uninterrupted manner. In this context, the degree of coverage refers to the macroscopic or technical aspect and means the area equipped with adhesive properties. If the adhesive is put on the lower film surface by a spray coating technique, the microscopic coverage may be far less than 90%, e.g. 10-30%. If less than 100% of the one surface is macroscopically covered with adhesive, this refers preferably to one or several non-adherent edges.

It is desired that the adhesive bandage film is made of breathable material or equipped with a large number of small holes or micropores of a size allowing vapor transfer. More specifically, the film including the adhesive layer should be vapor permeable and liquid impermeable. This means, the film including the adhesive is semipermeable. The property of vapor transmission is essential to allow continuous wearing of the adhesive film bandage for several days or even weeks. Otherwise moisture or sweat could accumulate under the film and promote adhesive debonding, skin macerations and bacterial infections. Vapour transmission is usually determined as moisture vapor transmission rate (MVTR). As the film is impermeable to water drops, patients can take showers at any time after the treatment, which contributes to a comfortable permanent wearing, even for some weeks.

There are various techniques to measure moisture vapor transmission rate (MVTR), also called water vapor transmission rate (WVTR), ranging from gravimetric techniques that measure the gain or loss of moisture by mass, to highly sophisticated instrumental techniques that in some designs can measure extremely low transmission rates. Note that special care has to be taken in measuring porous substances such as fabrics as some techniques are not appropriate. Likewise for very low levels, many techniques would not have the resolution to provide a reliable result. Numerous standard methods are described in ISO, ASTM, BS, DIN etc.—these are quite often industry-specific. Instrument manufacturers will often be able to provide test methods developed to fully exploit the specific design which they are selling. The condition under which the measurement is made has a considerable influence on the result. Both the temperature of and humidity gradient across the sample need to be measured, controlled and recorded with the result. An MVTR result without specifying these conditions is almost meaningless. Certainly no two results should be compared unless the conditions are known. The most common international unit for the MVTR is $g/m^2/day$. In the USA, $g/100in^2/day$ is also in use, which is approximately $\frac{1}{15}$ of the value of $g/m^2/day$ units. Typical rates in aluminium foil laminates may be as low as $0.001$ $g/m^2/day$, whereas the rate in fabrics can measure up to several thousand $g/m^2/day$. Often, testing is conducted on a sheet of material. Calculations based on that can be useful when designing completed structures (packages, clothing, etc). Seams and seals are also very important to end-use performance; performance verification and validation of complete containers or irregular objects is often recommended. For the present invention, the MVTR is measured according to the German DIN EN 13726.

The person skilled in the art knows how the quality of semipermeability of thin films is obtained by technically developing or adding very small perforations. For the present invention, the micropores have to be large enough to pass vapor but too small to pass water. When a polymeric material undergoes deformations to obtain micropores, it will lose stability and elasticity compared to the solid material, resulting in a loss of compression force. Therefore, the desired the moisture vapour transfer rate has to be reduced to a reasonable limit. Patients may have to be advised to refrain from sports and sauna during the wearing time to avoid sweating which could exceed the MVTR of the film bandage.

Summarizing the requirements of vapor transmission and compression force, the film layer including the adhesive according to the invention is defined to be vapor permeable with a moisture vapor transmission rate (MVTR) of 100-2000, preferably 300-1500, more preferably 500-1000 $g/m^2/24$ hrs/37° C. (10%-100% relative humidity) when measured according to DIN EN 13726.

Transparency is the physical property of allowing light to pass through the material without being scattered, which may be fulfilled to a large extent even by polymeric materials. For practical use, the demanded transparency of a polymeric film means that details behind it can be seen clearly. In particular, criteria may be the visibility of stratum corneum lines, epidermal ridges, or hairs. The composite according to the invention is substantially transparent, so changes of superficial target veins (skin irritation, changes of varicose veins) or unwanted skin reactions (inflammation, hematoma) can be visually checked while the film is in place. This means that the film and the adhesive are transparent. If a second release liner is used in particular embodiments, it also should be transparent to provide view on the application site and already attached parts of the bandage for proper placement. If elastic fibres are present, it is advantageous that these are likewise transparent. The person skilled in the art will appreciate, however, that even non-transparent fibres may be included into the composite without losing overall transparency since the fibres are usually very small or present at low concentration.

Due to transparency, the film bandage is almost invisible. As it is very thin, it can be worn invisibly even under tight clothing. Due to the minimal thickness and semipermeability the film does not develop heat accumulation like bandages do. Furthermore, it is a welcome feature of polymeric films to be waterproof. This feature is preferably preserved even when micropore techniques are applied during the production process. Also the adhesive is preferably water-resistant. In this case, the film bandage can be worn even when having a shower or when swimming. This means a big comfort for the patients. As the film bandage does not need renewal it also saves costs and time. These comfort factors increase patient compliance and thus improve the compression results (TABLE 1).

For most applications, it is desirable to have an adhesive bandage film being compatible with ultrasonic imaging. If ultrasound imaging can be applied while the bandage is in place, it is possible to inspect the compression effect and the healing process of the underlying disease. The transparency to ultrasound imaging implies that the film material including the adhesive is transparent to ultrasound waves to transfer signals without visible loss of energy. It furthermore implies that it is possible to attach the bandage film tightly to the skin without gas or air inclusions which would deteriorate the ultrasound signal.

While woven compression bandages do not allow any inspection of the pressure effects below, the compression film bandage offers both visual and ultrasonic controls. The person skilled in the art will appreciate that a definition by effect is more accurate than a definition by any mechanical parameters of the material.

For application as wrappable bandage, the film material may have a width of 6-50 cm, preferably 8-30 cm, more preferably 10-20 cm. For usual applications on a human body, the length may be 30-250 cm, preferably 100-225, more preferably 150-200 cm. Applications on very small body parts like fingers or on very large body parts like the chest or waist may require other dimensions. The shape will normally be rectangular with a length several times larger than the width. The ratio of length to width is preferably >10, more preferably >20. If the material is provided as a large sliceable roll for individual bandage lengths, the bandage film may have any reasonable length, for example 5 or 10 meters.

The film layer may be made of a material selected from polymeric substance like polyethylene, polypropylene, polyurethane, polyether urethane, polyether polyurethane, polyester urethane, polyether-polyamid-copolymers, polyester, Nylon, polyvinyl chloride polyacrylate, biopolymers and the respective fibres or films thereof.

The elasticity of the bandage film may be established by one single material, or by a compound of two or more. A basic elastic plastic film may contain additional longitudinal structures (e.g. fibres, bands) from a different material. Accordingly, the film layer or the adhesive may comprise elastic fibres which are preferably oriented in longitudinal direction. In another example, the film layer comprises or consists of an elastomer. Suitable elastomers are chosen from the polymer groups previously noted. An elastomer is a polymer with viscoelasticity (colloquially "elasticity"), generally having low modulus of elasticity and high failure strain compared with other materials. It is preferred that the fibres are transparent.

The film layer may comprise an indicator for stretching. The indicator enables one to observe or measure the extent of stretching of the film during application, to estimate or measure the degree of compression. For example, a meter scale may be imprinted into the film layer which can be measured against a second external scale or a scale imprinted on a detachable film carrier material. The indicator for stretching may also involve at least one of the release liners.

During application of the adhesive film compression bandage the film has to be separated from the one or several release liners. For this purpose, the release liner covering the adhesive side of the film should be adhering with an adhesive strength of less than 0.5 N/25 mm, optionally the first release liner may be provided with non-stick media, like silicon oil or wax, for easy removal.

During application of the compression film bandage, the adhesive layer has to be uncovered by removal of the first release liner. This removal has to occur in a longitudinal way, as the film has the shape of a bandage and the way of placement is in more or less narrow circles under longitudinal tension. During helical wrapping of body parts, at least a portion of the film bandage has to be uncovered which is usually less than one completed circle in length. The first release liner has to adhere just softly to the films lower surface, as it does not have to resist relevant stress except to stick to the film during storage and during unwinding of the film for application. In contrary, any significant adhesion would deteriorate easy application. Therefore, the optimal adhesive strength is in the range of 0.001-0.05, preferably 0.01-0.04, even more preferably 0.015-0.03 N/25 mm.

In one embodiment the second release liner is to be longitudinally removed after placement of the adhesive film on the target region. In this case, the requirements of the second release liner's adhesion to the film surface is approximately equal to that of the first release liner. In another embodiment when an elastic second release liner is used, it has to stand a higher stress compared to the first release liner. It has to stick to the film surface firmly even when the film with the second release liner in place is extended to full pre-tension before adapting it to the target. The required adhesive force is in the range of 0.01-0.2, preferably 0.02-0.15, even more preferably 0.03-0.1 N/25 mm.

For some applications, it may be convenient that the first release liner has separation means running along the width of the first release liner to provide separately removable release liner portions with a length of 1-12 times of the width of the release liner, preferably 2-8 times and more preferably 3-5 times. The separation means may consist of a continuous cut line or a perforation line or a non-connected overlapping area. The separation means are particularly useful for ripping the release liner off piece by piece during placement of the bandage film. For many applications, it is preferred that the first release liner comprises tab means to facilitate removal of the release liner. This is of particular advantage in case there are separation means as described above in order to facilitate removal of release liner portions. If present, the second release liner may also comprise one of the above separation means.

To facilitate longitudinal removal of the release liner or release liner portions at least one of the release liners may extend beyond the width or the length of the transparent film layer, or it may comprise tab means.

While the first release liner is substantially non-elastic, the second release liner may appear in different embodiments: In one embodiment the second release liner is non-elastic for longitudinal removal prior to adhering the film to the target, while in another embodiment the second release liner is elastic and expandable for removal after placement on the target. In this case, the restoration force of the elastic release liner is just 5-50%, preferably 10-25% of the film's restoration force. This limitation contributes to a proper placement without requiring too high forces to obtain the defined pre-tensions.

To fit to any region of the human body, the film has to be elastic in both longitudinal as to transversal directions. It has to be thin and flexible. Therefore it is demanded that the transparent film layer including an adhesive, optionally including the second release liner, is conformable to any anatomical surface.

To support easy storage and application, the composite may be wound around a role or cylindrical body.

For the same purpose, a dispenser may be used comprising the herein described composite. The dispenser comprises a roll of the composite of adhesive film and release liners according to the invention, and a mechanism for proper film deployment. The dispenser appears preferably in the form of a cylinder or a cylindrical body. The dispenser has at least one opening at one side which is big enough such that the composite or parts of it can be put through, but small enough such that the film compound roll will be retained in the box.

(21) The dispenser may also comprise means to exercise a certain resistance against winding off the composite such that the composite can be wrapped with a desired tension. Preferably, winding off is prevented up to forces of 3.0 N.

The dispenser may also comprise means for separating the film from one or several backings, or parts of them. The mechanism can include means to retain or collect one or several release liners or parts of them. Furthermore, the dispenser may comprise cutting elements in order to cut off single portions or redundant parts of the film, the release liners, or of all components.

All claims relating to the compression film bandage and all claims relating to the dispenser apply also for use as a medicament. The claims furthermore apply in particular for use in treating venous diseases or tissue lesions. As a priority, they apply for use in treating varicose veins.

EXAMPLE

Use of a transparent compression bandage in the treatment of varicose veins.

The bandage applied consisted of a polyurethane membrane of 25 microns thickness and >50 pores/mm$^2$ of <30 microns in diameter, coated with a layer of an acrylic adhesive. The film was attached in separate circles overlapping for about 2 cm. Tensions during application were in the range of 4-5 N/mm$^2$.

The patient was treated for 14 days (FIG. 8).

Similar optical results were obtained by using semipermeable polyethylene food wrap film of 12 microns thickness, attached with <0.1 g/100 cm$^2$ liquid bandage spray containing acrylic copolymer. However, effects on deeper veins were less intense with this type of material.

Figure 9:

The compression bandage showed improved results, when compared to compression stocking (FIG. 9).

Figure 10:
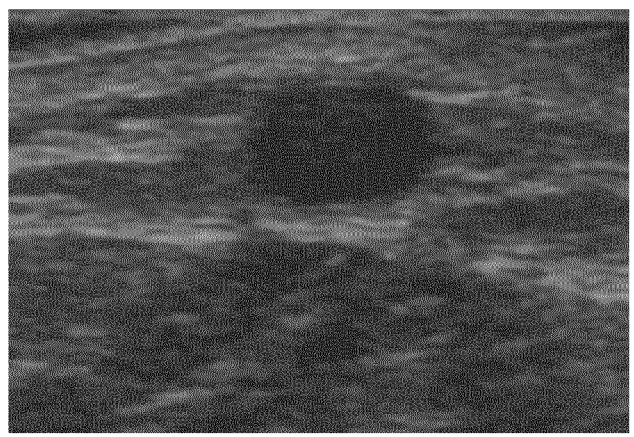
Figure 10:
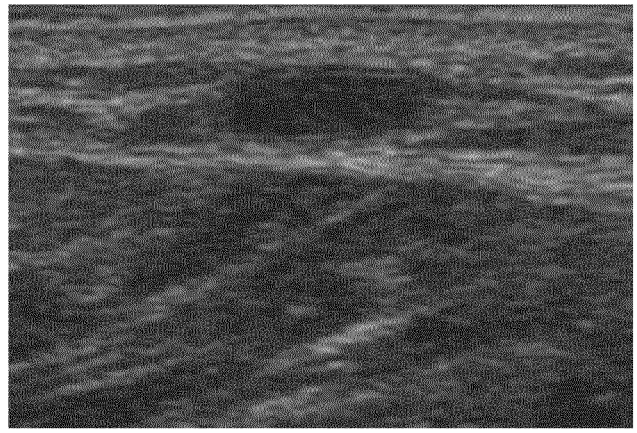

The results of the use of the transparent compression bandage are also visible in ultrasound imaging (FIG. 10).

FIGURE CAPTIONS

FIG. 1: Layers of the compression film bandage composite: a film layer (A), a medical adhesive (B) which is preferably pressure-sensitive coated on at least a portion of one surface of the film layer, a first release liner (C) covering the adhesive, and optionally, a second release liner (D) reversibly adhered to the upper film side to serve as a carrier, and optionally, perforations (e1, e2) and tab means (e2) of one or both release liners to ease the longitudinal removal.

FIG. 2a: Pattern of a leg cross section with varicose vein (A), with concentric compression (B) applied by arbitrary media. Conventional media like compression stockings or bandages and the novel adhesive compression bandage film do not differ much in the concentric compression effect, but they differ in the summary result due to the adhesive effect of the film. Furthermore, the compression film bandage can be worn 2 weeks or longer without interruption or exchange.

FIG. 2b: Pattern of a leg cross section with additional compression effect by the adhesive, discernible from the decreased vein diameter, when using a compression film bandage according to the invention.

Figure 3A:
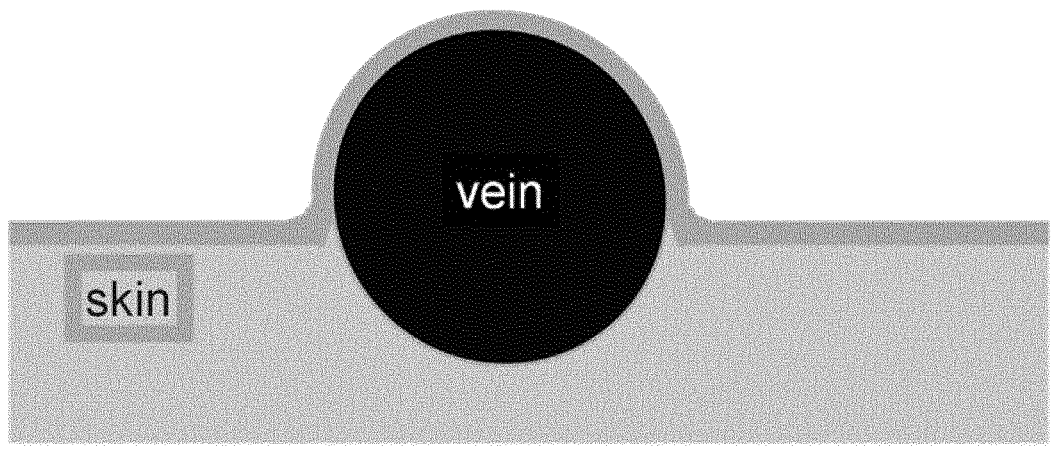

FIG. 3a: Detailed pattern of a superficial varicose vein bulging over skin level.

Figure 3B:
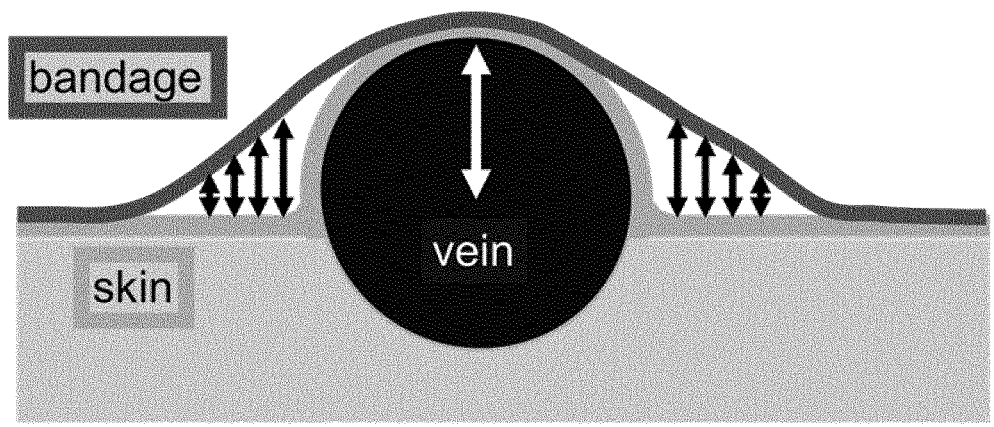

FIG. 3b: Gap areas (black arrows) resulting along superficial veins when using non-adhesive bandage media, due to the blood pressure (white arrow) enlarging varicosities in the standing patient. Strong adhesion could prevent this loss of effectivity.

Figure 3C:
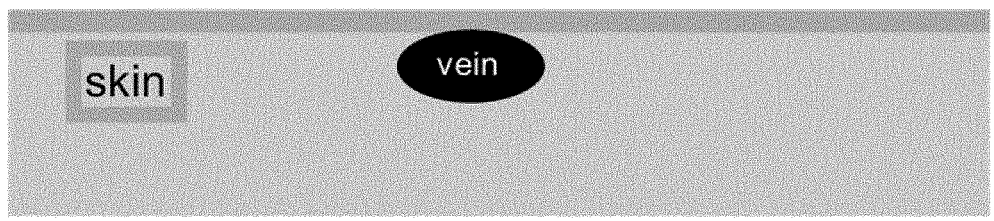
Figure 3D:
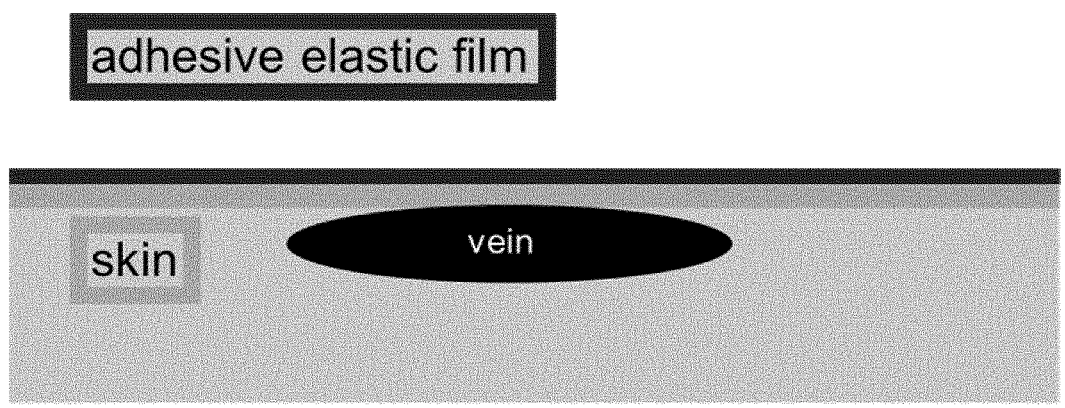
Figure 3E:
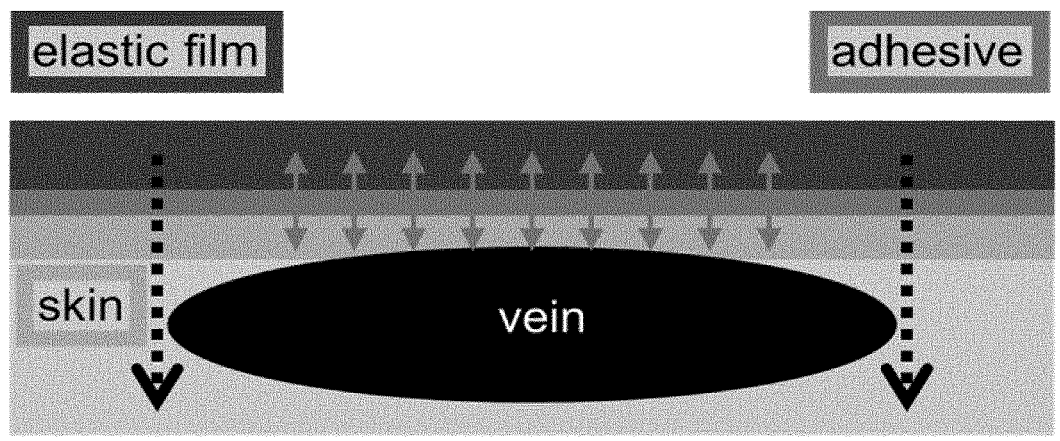

FIG. 3c: Pattern of the same superficial vein when the leg is elevated. The blood leaves the vein due to gravitation, and the vein shrinks to a minimum. This may be less than 20% of the size in the standing patient. The phenomenon is well known, as even legs severely diseased with varicosities look nicely when the leg is elevated.

FIG. 3d: When the adhesive compression film bandage is fixed on the elevated leg, it will keep the diseased vein small and under skin level even when the patient is in upright position.

FIG. 3e: Detailed pattern of the adhesive elastic film bandage, sticking firmly to the skin, forming a functional unit with the skin, executing a) concentric compression (dashed arrows) increasing the tissue pressure, and b) by the tight adhesive connection between film and skin (grey arrows), effectively limiting the space of the diseased vein to expand.

FIG. 4: Typical strain—elongation diagram of a compression film bandage according to the invention (B) in a. Y-axis: tension in N/mm$^2$; x-axis: elongation in %. Dashed straight line: Example for linear elasticity between 20 and 50% elongation. For the invention, the deviation of strain values to a linear progression should preferably not differ for more than 30% between 20 and 50% elongation (working range for film application, shaded area).

FIG. 5: ultrasound findings and corresponding scheme, 7 days after endoluminal occlusive vein therapy, A) when using textile bandage (short-stretch, standard in phlebology), showing a first thrombus formed at maximum compression effect (*), and evidence of a secondary re-entering blood and increase of diameter. Possible reasons: Discontinuation of bandage wearing, bandage exchange, loss of elasticity. Consequence: delay in vein regression. B) shows a similar vein after using a compression film bandage according to the invention, showing a homogenous echo signal without signs of re-entered blood.

FIG. 6: Comparison of a common elastic wound dressing (patch 10×10 cm, ruptured at 56% elongation) and an adhesive compression film bandage (acfb) according to the invention in a strain-elongation-diagram. Y-axis: tension in N/mm$^2$; x-axis: elongation in %.

FIG. 7: Comparison of the elastic behavior of common short-stretch bandages (A) and a compression film bandage according to the invention, 25 cm long samples each, (B) in a strain—elongation diagram. Y-axis: tension in N/mm$^2$; x-axis: elongation in cm.

FIG. 8: Photograph of a varicose vein before treatment (A), after 7 d (of 14) with adhesive compression bandage (B), final result (C).

FIG. 9: Polyurethane film at lower limb: Brownish discolorations along former vein course above film edge (arrows), no discolorations within film compressed zone. The whole leg had been covered by a medical compression stocking German class II. The film was worn for 10 days, patient took showers 7 times. Film edge was slightly damaged by friction mediated by stocking while walking.

FIG. 10: Identical spot of of lower limb in ultrasound imaging: a) non-compressed vein before application of compression film bandage, b) vein after positioning a polyurethane film bandage of 25 microns thickness and 100 mm width, one closed circle, acrylic glue, tension applied during application: 16-18 N/mm$^2$

The invention claimed is:

1. A film compression bandage composite using elastic forces combined with adhesive forces, for compression treatment of venous diseases and tissue lesions, comprising
   a. an elastic film with a modulus of elasticity of 5-400 N/mm$^2$, when applying longitudinal expansions of 10-100%, and producing tensions of 1-40 N/mm$^2$,
   b. a medical adhesive coated on at least a portion of a lower surface of the elastic film, which is pressure-sensitive and hypoallergenic, configured to adhere to an upper surface of the elastic film with an adhesive force of 0.12-2 N/25 mm, and configured to adhere to human skin with an adhesive force of 0.06-1 N/25 mm measured after 24 hours of wearing; and
   c. a first release liner covering the medical adhesive coating, for longitudinal removal, wherein the lower surface of the elastic film is coated homogenously and in an uninterrupted manner by the medical adhesive coating, and wherein the elastic film is transparent to ultrasonic imaging.

2. The composite of claim 1, further comprising a second release liner adhering to the upper surface of the elastic film, and configured to be removed prior to adhering of the medical adhesive coating.

3. The composite of claim 2, wherein the second release liner
   a. is inelastic, wherein the second release liner is configured to adhere to the upper surface of the elastic film with an adhesive force of 0.001-0.05 N/25 mm, or
   b. is elastic, wherein the second release liner comprises an adhesive strength of 0.01-0.2 N/25 mm.

4. The composite according to claim 1, wherein the elastic film has a modulus of elasticity of 10-200 N/mm² when applying longitudinal expansions of 10-100% and producing tensions of 1-40 N/mm².

5. The composite of claim 1, wherein a tensile strength of the elastic film is 5-50N/25 mm.

6. The composite of claim 1, wherein the elastic film is 5-50 microns in thickness.

7. The composite of claim 1, wherein the elastic film is vapor permeable with a moisture vapor transmission rate (MVTR) of 100-2000 g/m²/24 hrs/37° C. (10%-100% relative humidity) when measured according to the test methods for primary wound dressings set forth in European Standard EN 13726.

8. The composite of claim 1, wherein the elastic film or the medical adhesive coating comprises elastic fibres or elastomeric elements in a longitudinal orientation.

9. The composite of claim 1, wherein the elastic film comprises an indicator for stretching.

10. The composite of claim 1, wherein the first release liner comprises an adhesive strength of 0.001-0.05 N/25 mm.

11. The composite of claim 1, wherein the first release liner has separation means running along the width of the first release liner to provide separately removable release liner portions with a length of 1-12 times of the width of the first release liner.

12. The composite of claim 1, wherein the first release liner is non-elastic.

13. A dispenser comprising a roll of the film compression bandage composite according to claim 1.

14. A method of treating a condition, comprising applying the film compression bandage composite of claim 1 to a patient.

15. A method of treating venous diseases, tissue lesions or varicose veins, the method comprising applying the film compression bandage composite of claim 1 to a patient.

16. A method for treating varicose veins, comprising applying the film compression bandage composite of claim 1 to a patient.

* * * * *